United States Patent
Widzgowski

(10) Patent No.: US 10,073,034 B2
(45) Date of Patent: Sep. 11, 2018

(54) METHOD FOR MEASURING THE LIFETIME OF AN EXCITED STATE IN A SAMPLE

(71) Applicant: Leica Microsystems CMS GmbH, Wetzlar (DE)

(72) Inventor: Bernd Widzgowski, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 772 days.

(21) Appl. No.: 13/676,408

(22) Filed: Nov. 14, 2012

(65) Prior Publication Data
US 2013/0119276 A1 May 16, 2013

(30) Foreign Application Priority Data

Nov. 14, 2011 (DE) .................... 10 2011 055 330

(51) Int. Cl.
*G01J 1/58* (2006.01)
*G01N 21/64* (2006.01)

(52) U.S. Cl.
CPC ..... *G01N 21/6408* (2013.01); *G01N 21/6458* (2013.01); *G01N 2201/0697* (2013.01); *G01N 2201/12* (2013.01)

(58) Field of Classification Search
CPC ............... G01N 21/64; G01N 21/6408; G01N 2021/6421; G01N 21/6458; G01N 21/6428

(Continued)

(56) References Cited

U.S. PATENT DOCUMENTS 5,909,278 A * 6/1999 Deka et al. ................... 356/318
5,981,957 A 11/1999 Cruce
(Continued)

FOREIGN PATENT DOCUMENTS

DE   3110943 A1   9/1982
DE   3732217 A1   4/1988
(Continued)

OTHER PUBLICATIONS

Lakowicz, J. R., "Principles of Fluorescence Spectroscopy", Third Edition, Chapters 4 & 5, Springer Science +Business Media, LLC.
(Continued)

*Primary Examiner* — David Porta
*Assistant Examiner* — Mamadou Faye
(74) *Attorney, Agent, or Firm* — Patentbar International, P.C.

(57) ABSTRACT

The present invention relates to a method for measuring the lifetime of an excited state in a sample, in particular a fluorescence lifetime, and to an apparatus for carrying out such a method. First, an excitation pulse is generated and a sample region is illuminated with the excitation pulse. Then, a first digital data sequence is generated which is representative of the power-time profile of the excitation pulse, and a first switching instant is determined from the first digital data sequence. Moreover, the detection light emanating from the sample region is detected by a detector, and a second digital data sequence is generated which is representative of the power-time profile of the detection light, and a second switching instant is determined from the second digital data sequence. Finally, the time difference between the first and second switching instants is calculated.

35 Claims, 6 Drawing Sheets

(58) Field of Classification Search
USPC ................................................. 250/459.1
See application file for complete search history.

(56) References Cited

U.S. PATENT DOCUMENTS

| | | | |
|---|---|---|---|
| 6,137,584 A * | 10/2000 | Seidel et al. | 356/445 |
| 6,317,207 B2 * | 11/2001 | French et al. | 356/317 |
| 2002/0063863 A1 | 5/2002 | Kask | |
| 2004/0007675 A1 | 1/2004 | Gillispie et al. | |
| 2004/0189504 A1 * | 9/2004 | Dasgupta | H03M 1/144 |
| | | | 341/156 |
| 2005/0036150 A1 | 2/2005 | Izatt et al. | |
| 2005/0136448 A1 | 6/2005 | Hartel et al. | |
| 2006/0134644 A1 * | 6/2006 | Hartel | C12Q 1/6816 |
| | | | 435/6.12 |
| 2007/0259451 A1 | 11/2007 | Heanue et al. | |
| 2007/0260145 A1 * | 11/2007 | Heanue et al. | 600/473 |
| 2008/0007820 A1 * | 1/2008 | Moehler | G02B 21/008 |
| | | | 359/363 |
| 2008/0025462 A1 * | 1/2008 | Sutko et al. | 378/44 |
| 2009/0212769 A1 | 8/2009 | Stoica et al. | |
| 2012/0032095 A1 * | 2/2012 | Nicholls | G01N 21/6408 |
| | | | 250/459.1 |
| 2013/0019084 A1 * | 1/2013 | Orchard et al. | 712/222 |
| 2013/0084649 A1 * | 4/2013 | Crane | G01N 21/6408 |
| | | | 436/501 |

FOREIGN PATENT DOCUMENTS

| | | |
|---|---|---|
| DE | 4339784 A1 | 5/1995 |
| DE | 4339787 C2 | 5/1995 |
| DE | 4420572 C2 | 12/1995 |
| DE | 102004017956 A1 | 11/2005 |
| DE | 102008004549 A1 | 7/2009 |
| DE | 19681741 B4 | 5/2011 |
| EP | 0927366 B1 | 7/1999 |
| EP | 1291627 A1 | 3/2003 |
| WO | 19980023941 A2 | 6/1998 |
| WO | 2010045400 A2 | 4/2010 |

OTHER PUBLICATIONS

Anonymous: "Which Fluorescence Lifetime System is Best for You?", SPEX Fluorescence Group Application Notes F-10, Jan. 1, 2004, Horiba Group, Jobin Yvon, Inc, http://www.horiba.com/fileadmin/uploads/Scientific/Documents/Fluorescence/F-10.pdf.

Vandeven et al, Pitfalls and Their Remedies in Time-Resolved Fluorescence Spectroscopy and Microscopy, Journal of Fluorescence, May 2005, pp. 377-413, v. 15, No. 3.

* cited by examiner

METHOD FOR MEASURING THE LIFETIME OF AN EXCITED STATE IN A SAMPLE

RELATED APPLICATIONS

This application claims priority to German Patent Application No. 10 2011 055 330.4, filed Nov. 14, 2011, which is incorporated herein by reference in its entirety.

FIELD OF THE INVENTION

The present invention relates to a method for measuring the lifetime of an excited state in a sample, in particular a fluorescence lifetime, and to an apparatus for carrying out such a method.

The present invention also relates to an apparatus for measuring the lifetime of an excited state in a sample, in particular a fluorescence lifetime, the apparatus including a light source for generating an excitation pulse for illuminating a sample region with the excitation pulse and a detector for detecting the detection light emanating from the sample region.

BACKGROUND OF THE INVENTION

By analyzing the lifetime of the excited states of a sample labeled with one or more fluorescent dyes, important information can be obtained about the properties of the sample. Especially when multiple fluorescent dyes are used, information about a sample region being analyzed, such as information about the composition and surroundings thereof, can be obtained using fluorescence lifetime imaging microscopy (FLIM). In cell biology, for example, the calcium concentration in a sample region can be indirectly inferred by measuring the lifetime of the fluorescent dyes.

There are a number of methods for measuring the lifetime of the excited states of fluorescent dyes. Some of these methods are described in detail in Chapters 4 and 5 of the textbook by Joseph R. Lakowicz entitled "Principles of Fluorescence Spectroscopy," Kluwer Academic/Plenum Publishers, 2nd ed., 1999. For example, it is possible to modulate the power of the excitation light over time so that conclusions about the lifetime of the excited state can be drawn from the phase delay of the emitted light.

It is also possible to excite the fluorescent dyes with short light pulses so that the time delay of the emission pulses can be measured electronically. German Patent Publication DE 10 2004 017 956 A1, for example, describes a microscope for analyzing the lifetime of excited states in a sample, which includes at least one light source for generating excitation light and at least one detector for receiving detection light emanating from the sample. The microscope is characterized in that the light source includes a semiconductor laser which emits pulsed excitation light, and that an adjusting device is provided for adjusting the pulse repetition rate to the specific lifetime properties of the sample.

In particular, the electronics required for data analysis is commercially available, often in the form of PC plug-in cards. However, apart from the high cost, such a time measurement card has the disadvantage of a very long dead time, so that, upon excitation of the sample, it can only detect the arrival of the first detection pulse (first detection photon) and is then "blind" for a significant period of time. Ultimately, a significant portion of the information contained in the detection light emanating from the sample remains hidden from the user.

Moreover, it is not possible to achieve a high repetition rate for the excitation pulses and, therefore, it is also not possible to perform frequent measurements within one measurement period. The actually achievable measurement rate is far below the usual repetition rates of commercially available pulsed lasers. For this reason, it usually takes a very long time until sufficient data is collected, for example, to generate a FLIM image.

SUMMARY OF THE INVENTION

It is, therefore, an object of the present invention to provide a method that makes it possible to obtain more accurate measurement results in less time.

This object is achieved by a method including the following steps:
a. generating an excitation pulse and illuminating a sample region with the excitation pulse,
b. generating a first digital data sequence which is representative of the power-time profile of the excitation pulse,
c. determining a first switching instant from the first digital data sequence,
d. detecting the detection light emanating from the sample region by means of a detector,
e. generating a second digital data sequence which is representative of the power-time profile of the detection light,
f. determining a second switching instant from the second digital data sequence, and
g. calculating the time difference between the first and second switching instants.

It is a further object of the present invention to provide an apparatus that makes it possible to obtain more accurate measurement results in less time.

This further object is achieved by an apparatus of the above-mentioned type, including a control device
a. which generates a first digital data sequence which is representative of the power-time profile of the excitation pulse,
b. which determines a first switching instant from the first digital data sequence,
c. which generates a second digital data sequence which is representative of the power-time profile of the detection light,
d. which determines a second switching instant from the second digital data sequence, and
e. which calculates the time difference between the first and second switching instants.

In accordance with the present invention, it was discovered, inter alia, that additional information beyond the time of arrival of the first photon can be obtained only if the signal-processing control device is capable of also detecting those photon events which occur after the arrival of the first photon, but belong to the same excitation pulse. It was also discovered that this can be achieved by converting the analog measurement signals immediately into sequences of digital numbers.

The present invention advantageously enables, in particular, cyclically repeated measurements at a repetition frequency of 80 MHz and above, which corresponds to that of commercially available pulsed lasers. Moreover, more accurate information can be obtained about the lifetime characteristics of the sample since—in particular due to the high data processing speed—not only the time of arrival of the first photon is detected at any one time, but nearly all photon events, provided there is sufficient excitation power.

In one specific embodiment of the method, it is provided that the excitation pulse originates from a primary light pulse, a portion of which is delivered to an excitation detector which generates a first analog electrical signal whose amplitude-time profile is dependent on the time profile of the power of the portion of the primary light pulse, and that in order to generate the first digital data sequence, the first analog electrical signal is sampled over time, in particular in predefined and/or predefinable first time slots.

In particular, it may be provided that the light source generates a primary light beam which is split by a beam splitter into an excitation beam, which includes the excitation pulses, and a measurement beam, and that an excitation detector receives the measurement beam and generates a first analog electrical signal whose amplitude-time profile is dependent on the time profile of the power of the measurement beam, and that in order to generate the first digital data sequence, the control device samples the first analog electrical signal over time, in particular in predefined and/or predefinable first time slots.

Particularly fast generation of the first data sequence can be achieved, for example, by generating the first data sequence from standardized electrical signals, in particular binary digits, in such a way that either a lower standardized signal (e.g., "0") is generated when the amplitude just sampled is below a defined and/or definable first excitation threshold, or an upper standardized signal which is different from the lower standardized signal (e.g., "1") is generated when the amplitude just sampled is above a defined and/or definable second excitation threshold.

Advantageously, it may be provided that the detector generates a second analog electrical signal whose amplitude-time profile is dependent on the time profile of the power of the detection light, and that in order to generate the second digital data sequence, the second analog electrical signal is sampled over time, in particular in predefined and/or predefinable second time slots.

Analogously to the first data sequence, it may be provided that the second data sequence is generated from standardized electrical signals, in particular binary digits, in such a way that either a lower standardized signal is generated when the amplitude just sampled is below a defined and/or definable first detection threshold, or an upper standardized signal which is different from the lower standardized signal is generated when the amplitude just sampled is above a defined and/or definable second detection threshold.

To be able to detect, to the extent possible, all photon events, it is provided in an advantageous embodiment that, in order to generate data sequences, the first and/or the second analog electrical signal is sampled—in particular by a control device—at a sampling frequency which is significantly higher than the repetition frequency. In particular, it may be provided that the first and/or the second analog electrical signal is sampled at a sampling frequency more than 50 times, in particular more than 100 times higher than the repetition frequency. In a particularly advantageous embodiment, the first and/or the second analog electrical signal is sampled at a sampling frequency about 125 times higher than the repetition frequency. In one particular embodiment, the first and/or the second analog electrical signal is sampled at a sampling frequency of 10 GHz, while the repetition frequency is 80 MHz.

In a particular embodiment, in order to further increase the time resolution, the first and/or the second analog electrical signal is sampled repeatedly. In particular, it may be provided that the first and/or the second analog electrical signal is sampled repeatedly, but with an—in particular continuously adjustable—time offset which is shorter than a time slot.

In a particularly advantageous embodiment which provides particularly accurate results, the first and/or the second analog electrical signal is sampled n times, but with a time offset that corresponds to the n-th fraction of a time slot. For example, in the case of double sampling, the time offset to be provided would accordingly be half the duration of a time slot.

Preferably, the sampling results of the multiple samplings are then mathematically combined, in particular interleaved, to produce the first data sequence and the second data sequence, respectively. In particular, by multiple sampling and mathematical combination, it is possible to produce a data sequence that contains n times more data, and thus has a significantly higher information content, than would be obtained by single sampling for the same measurement period.

Particularly fast and reliable generation of the first digital data sequence is possible when using, for example, a first sampling device including a comparator and/or a constant fraction discriminator. This makes it possible, in particular, to achieve sampling rates in the range of several 10 Gbits, for example, of 28 Gbits, without difficulty. The same applies with respect to the generation of the second digital data sequence, which is advantageously performed using a second sampling device, which also includes a comparator and/or a constant fraction discriminator. The sampling rates may be the same, but do not necessarily have to be the same. Rather, depending on the particular application, the sampling rate for generating the first digital data sequence may differ from the sampling rate for generating the second digital data sequence.

In an advantageous embodiment of the method, the first data sequence is converted into first parallel data words and/or the second data sequence is converted into second parallel data words. In particular, a first serial-to-parallel converter may be provided to convert the first data sequence into first parallel data words. Alternatively, or in addition, a second serial-to-parallel converter may be provided to convert the second data sequence into second parallel data words. Such an embodiment has the particular advantage that the data words can be rapidly and efficiently processed further in parallel-operating evaluation electronics.

In particular, the first and/or the second serial-to-parallel converter may advantageously generate data words which are each representative of a measurement period that is at least as long as the time interval between successive excitation pulses.

It is particularly advantageous if the first and/or the second serial-to-parallel converter generates data words which are representative of a measurement period that is exactly as long as the time interval between successive excitation pulses because then, all information pertaining to a measurement cycle associated with an excitation pulse is combined into one data word at any one time. This facilitates handling of the data and increases the speed and efficiency of the analysis.

Advantageously, it may be provided that the first switching instant is defined—in particular by a control device—to be the instant at which there is a change from a lower standardized signal to an upper standardized signal or a change from an upper standardized signal to a lower standardized signal within the first data sequence and/or within a first data word. This way of determining the switching instant is particularly rapid.

Alternatively, it may be provided that the first switching instant is defined—in particular by a control device—to be the instant which is calculated from the instant of a first change from a lower standardized signal to an upper standardized signal and from the instant of a second change from an upper standardized signal to a lower standardized signal within the first data sequence and/or within the first data word, and doing so, in particular, by calculating the arithmetic mean of the time intervals between the changes. This way of determining the switching instant is particularly accurate.

Analogously, the second switching instant may be defined in the same way, namely in that the second switching instant is defined to be the instant at which there is a change from a lower standardized signal to an upper standardized signal or a change from an upper standardized signal to a lower standardized signal within the second data sequence and/or within a second data word.

Alternatively, it may be provided also for the determination of the second switching instant, that it is calculated—in particular by a control device—from the instant of a first change from a lower standardized signal to an upper standardized signal and from the instant of a second change from an upper standardized signal to a lower standardized signal within the second data sequence and/or within a second data word, and doing so, in particular, by calculating the arithmetic mean of the time intervals between the changes.

Particularly precise information about the properties of the sample region to be analyzed can be obtained by generating at least one frequency distribution of a plurality of calculated time differences. The frequency distribution may be used, for example, in the generation of a FLIM image of the sample.

In particular in order to generate a fluorescence lifetime image, it may be provided that different sample regions, in particular ones which are adjacent to each other and/or disposed adjacent to each other in a scan line, are sequentially analyzed one after the other with respect to the lifetime of an excited state. For further data analysis, it is particularly advantageous to add position information to the data sequences and/or data words and/or frequency distributions and/or time differences of each sample region.

To be able to analyze different, in particular adjacent, sample locations sequentially one after the other—in particular for scanning a sample—it is advantageous to use a scanning device for steering the excitation light and/or the detection light. The scanning device may include one or more tilting mirrors whose rotational position is adjustable, for example, by means of galvanometers.

In a particularly advantageous embodiment, a scanning device is provided for directing the excitation light to different sample locations and/or for scanning a sample, the control device adding position information regarding the particular position of the scanning device to the data sequences and/or data words and/or frequency distributions and/or time differences of each sample region. A fluorescence lifetime image can be generated from this data in a particularly rapid and efficient manner.

In an embodiment that is particularly reliable and rapid in operation, the control device and/or at least one sampling device and/or at least one of the serial-to-parallel converters forms part of a programmable integrated circuit, in particular a field programmable gate array (in short: FPGA). Such an embodiment has the additional advantage that it particularly readily adaptable to individual boundary conditions.

In an advantageous embodiment, the apparatus of the present invention forms part of a scanning microscope, in particular a confocal scanning microscope.

BRIEF DESCRIPTION OF THE DRAWINGS

Other objectives, advantages, features and possible applications of the present invention may be derived from the following description of an exemplary embodiment, which makes reference to the drawing. In this context, all of the described and/or illustrated features constitute the subject matter of the present invention, either alone or in any useful combination, and regardless of the manner in which they are combined in the claims or antecedents thereof.

In the drawing.

DETAILED DESCRIPTION OF THE PREFERRED EMBODIMENTS

Figure 1:
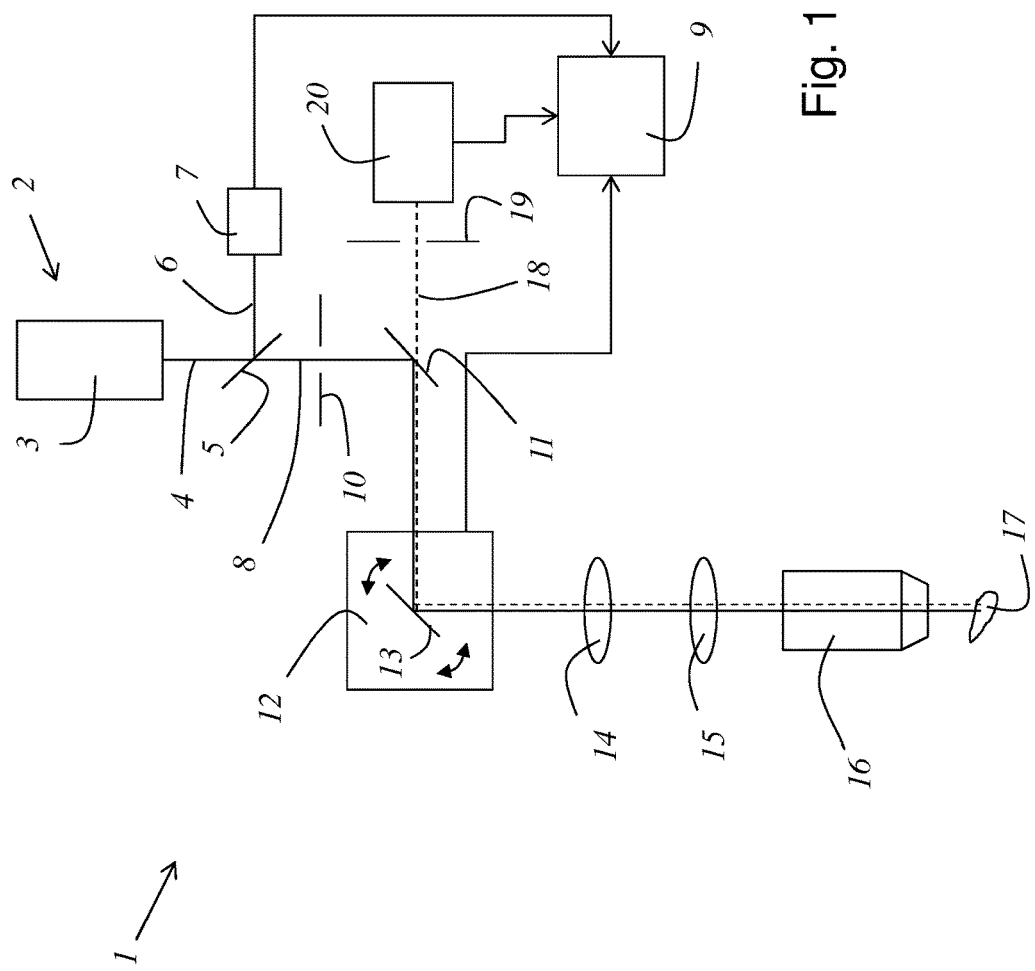
FIG. 1 depicts an exemplary embodiment of a scanning microscope that includes an apparatus according to the present invention.

FIG. 1 shows an exemplary embodiment of a scanning microscope that includes an apparatus according to the present invention. Scanning microscope 1 is in the form of a confocal scanning microscope.

Scanning microscope 1 has a light source 2 in the form of a pulsed laser 3 adapted to produce a rapid sequence of excitation pulses. Specifically, pulsed laser 3 produces a primary light beam 4 which strikes a first beam splitter 5. There, primary light beam 4 is split into a measurement beam 6 and an excitation beam 8. Measurement beam 6 is directed onto an excitation detector 7. Excitation detector 7 generates a first analog electrical signal whose amplitude-time profile is proportional to the time profile of the power of excitation beam 8. The first analog electrical signal is delivered to a control device 9, which generates therefrom a first digital data sequence which is representative of the power-time profile of excitation light 8.

Excitation beam 8 passes through an illumination pinhole 10, and then reaches main beam splitter 11. The main beam splitter directs excitation beam 8 toward a scanning device 12 including a gimbal-mounted scanning mirror 13. Then, excitation beam 8 passes through scanning optics 14, tube optics 15, and through microscope objective 16, and reaches sample 17. There, a sample region is exposed to the excitation light, thereby optically exciting the fluorescent dyes present there.

The detection light 18 emanating from the sample reaches main beam splitter 11 along the same optical path along which excitation beam 8 traveled from main beam splitter 11 to sample 17, but in opposite direction, then passes through the main beam splitter and the downstream detection pinhole 19, and finally reaches a detector 20.

Detector 20 generates a second analog electrical signal whose amplitude-time profile is dependent on the time profile of the power of detection light 18. The second analog electrical signal is also delivered to control device 9. There, in order to generate the second digital data sequence, the second analog electrical signal is sampled over time in predefined second time slots. In this connection, as will be explained in greater detail in the following exemplary embodiments, control device 9 generates the second data sequence in time correlation with the first data sequence.

Scanning device 12 delivers to control device 9 information regarding the particular position of scanning mirror 13. Control device 9 correlates this information with the respective data obtained from the first analog signal and the second analog signal in a manner that makes it possible to infer which sample location the data belongs to.

Figure 2:
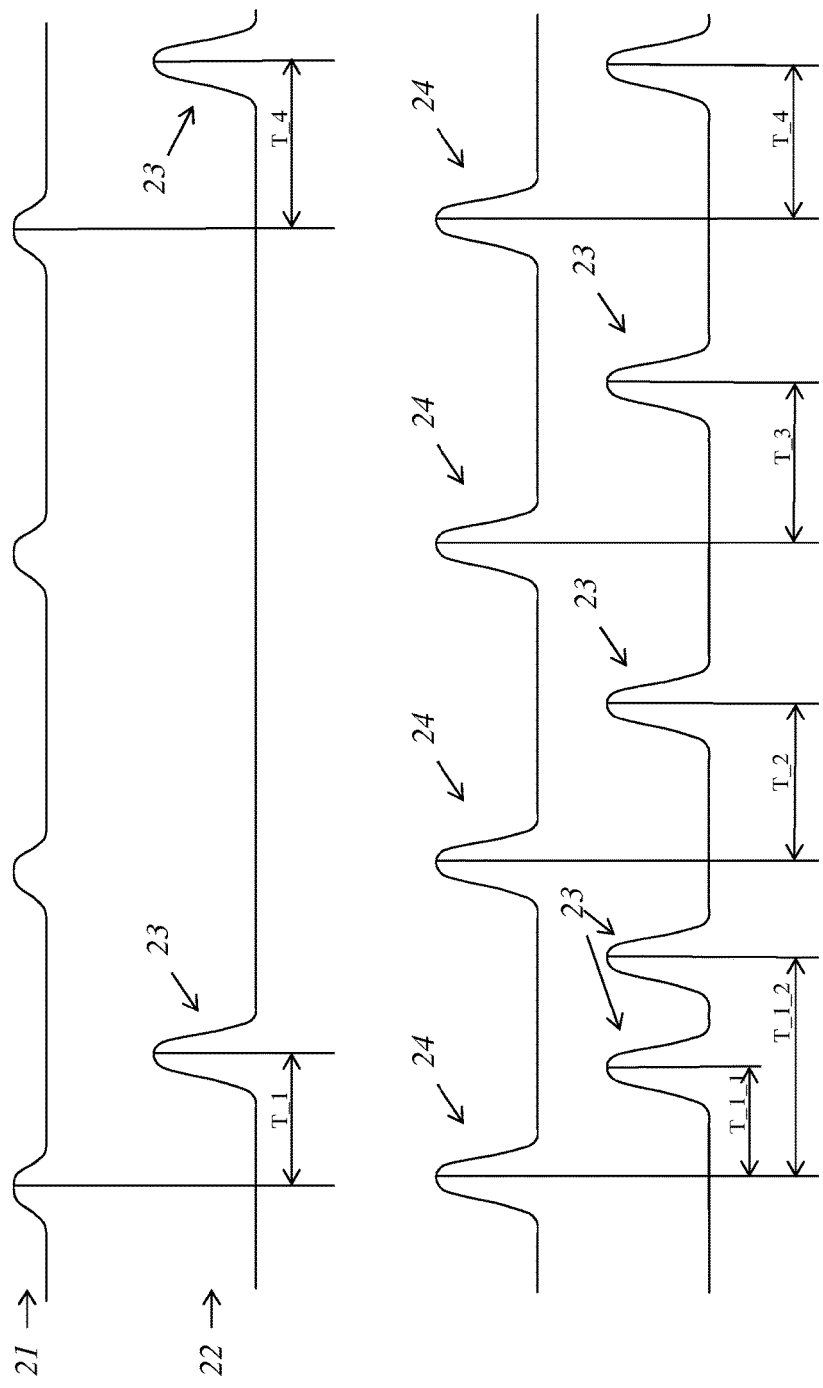
FIG. 2 shows the power-time profiles of the excitation light and the detection light at very low excitation power and at high excitation power.

FIG. 2 shows, in its upper half, the power-time profile of excitation light 21 and the power-time profile of detection light 22 at very low excitation power. It can be seen that only a few photon events 23 can be captured and detected because of the low emission probability, which is due to the low power of the excitation light. Such a measurement situation can still be handled by prior art apparatus. However, this is not true for the situation shown in the lower half of the figure (high excitation power).

In the case of a high excitation power, the emission probability is so high that one excitation pulse 24 may even trigger several photon events 23. The generation of a fist digital data sequence 25 and a second digital data sequence 26 is illustrated in FIGS. 3 and 4.

Figure 3:
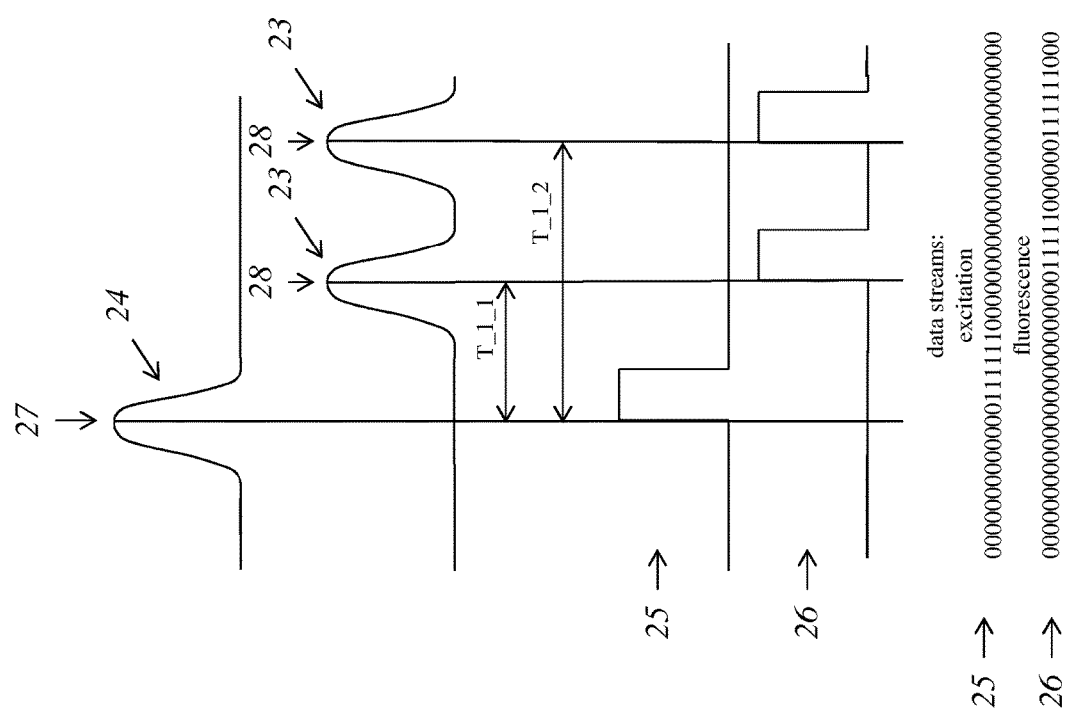
FIG. 3 shows the time profiles of the excitation light and the detection light, as well as a representation of the digital data sequences in a possible embodiment.
Figure 4:
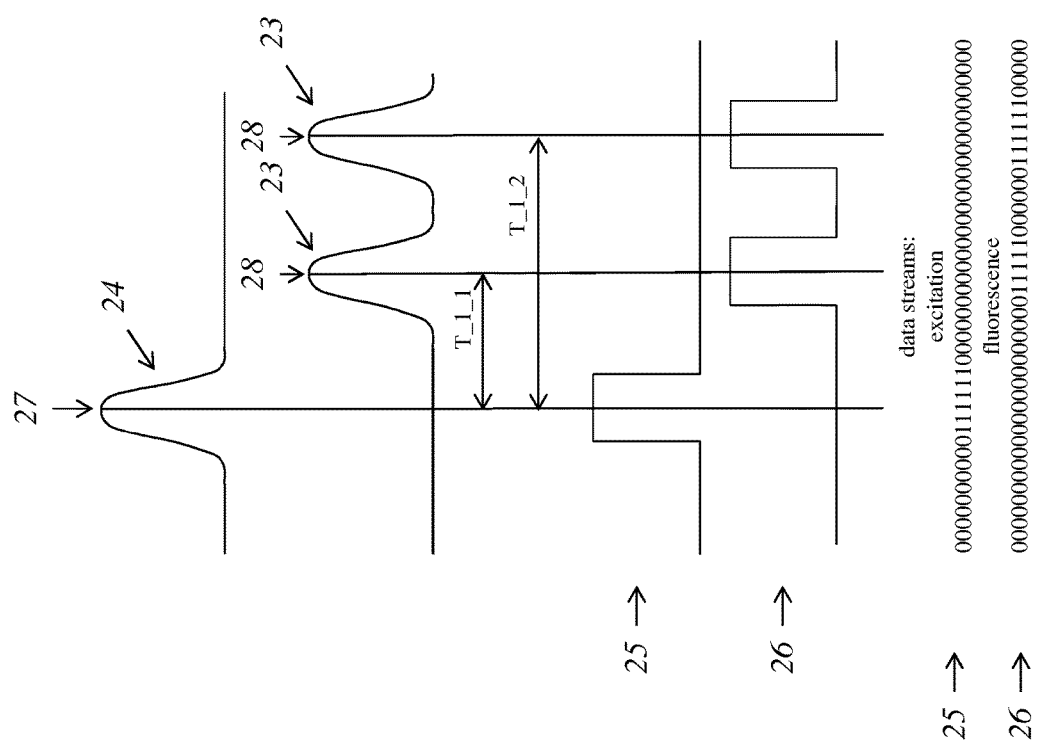
FIG. 4 shows the time profiles of the excitation light and the detection light, as well as a representation of the digital data sequences in another possible embodiment.

FIG. 3 and FIG. 4 show embodiments where digital data sequences 25, 26 are generated from standardized electrical signals, namely binary digits 0 and 1, and in such a way that either a lower standardized signal, namely 0, is set when the amplitude just sampled is below a defined and/or definable first excitation threshold, or an upper standardized signal, namely 1, is set when the amplitude just sampled is above a defined and/or definable second excitation threshold. The thresholds may be the same, but do not necessarily have to be the same.

In the embodiment shown in FIG. 3, the first switching instant 27 is defined—in particular by a control device 9—to be the instant at which there is a change from a lower standardized signal, namely 0, to an upper standardized signal, namely 1, within first data sequence 25 and/or within the first data word.

Analogously, with respect to second data sequence 26, second switching instants 28 are defined to be the instants at which there is a change from a lower standardized signal, namely 0, to an upper standardized signal, namely 1, within second data sequence 26 and/or within a second data word.

FIG. 4 shows another embodiment which is advantageous for use with constant fraction discriminators. In this embodiment, first switching instant 27 is defined—in particular by a control device 9—to be the instant that is calculated as an arithmetic mean from the instant of a first change from a lower standardized signal to an upper standardized signal and from the instant of a second change from an upper standardized signal to a lower standardized signal within first data sequence 25 and/or within a first data word. Analogously, second switching instants 28 are also calculated as arithmetic means of the instants of the corresponding changes within second data sequence 26.

Figure 5:
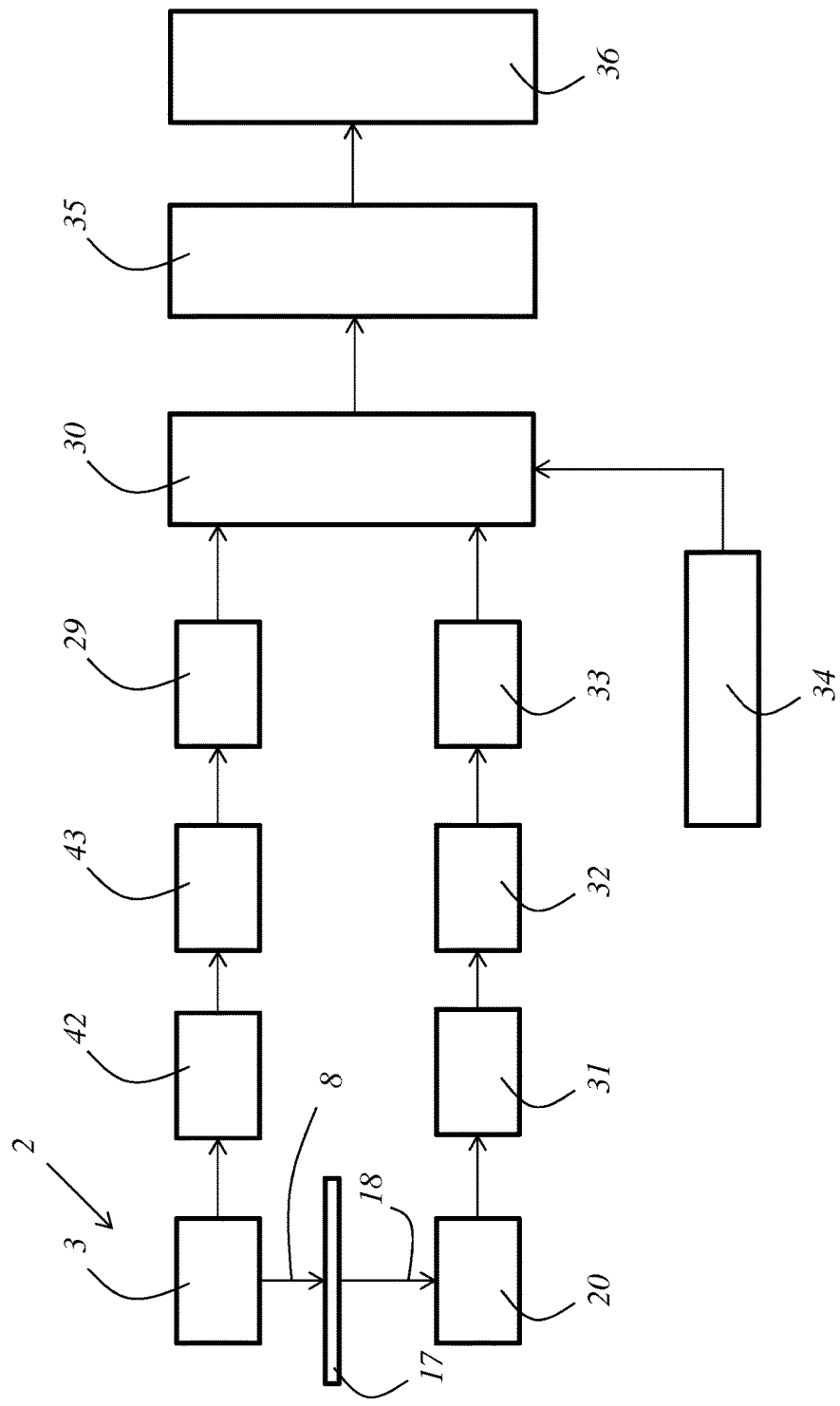
FIG. 5 shows an exemplary embodiment in schematic form.

FIG. 5 illustrates an exemplary embodiment in a schematic representation where the individual components are shown as boxes for purposes of clarity. A sample 17 is illuminated with illuminating light 8 from a light source 2 in the form of a pulsed laser 3. At the same time, a first analog electrical signal is generated whose amplitude is proportional to the power of illuminating light 8. The first analog electrical signal is delivered to a first constant fraction discriminator 42 for signal conditioning. The conditioned first analog electrical signal is then passed on to a first comparator 43, which generates a first digital data sequence by sampling the first analog signal over time.

The first digital data sequence is delivered to a serial-to-parallel converter 29, which generates first parallel data words. The data words are in each case representative of a measurement period that is exactly as long as the time interval between successive excitation pulses. The data words are then delivered to a correlating unit 30.

A detector 20 receives detection light 18 emanating from sample 17 and generates a second analog electrical signal which is delivered to a second constant fraction discriminator 31 for signal conditioning. The conditioned second analog electrical signal is then passed on to a second comparator 32, which generates a second digital data sequence by sampling the second analog signal over time. The second digital data sequence is delivered to a second serial-to-parallel converter 33, which generates second parallel data words. The second data words are in each case representative of a measurement period that is exactly as long as the time interval between successive excitation pulses. The second data words are then also delivered to a correlating unit 30.

A scan control unit 34 delivers to correlating unit 30 pixel data that is associated with the sample region being examined.

Correlating unit 30 correlates the first data words, the second data words and the pixel data with each other within data packets. The data packets are then delivered to a unit 35 for determining the switching instants and for calculating the time difference between the first and second switching instants. In addition, a frequency distribution of the time difference is also calculated in each case in unit 35. The calculated data and information are transferred to a memory 36 and stored therein. It is possible to further analyze the data and information off-line at a later time. Alternatively, or in addition, the data may be displayed to the user on-line during the experiment, for example, in the form of a FLIM image.

Figure 6:
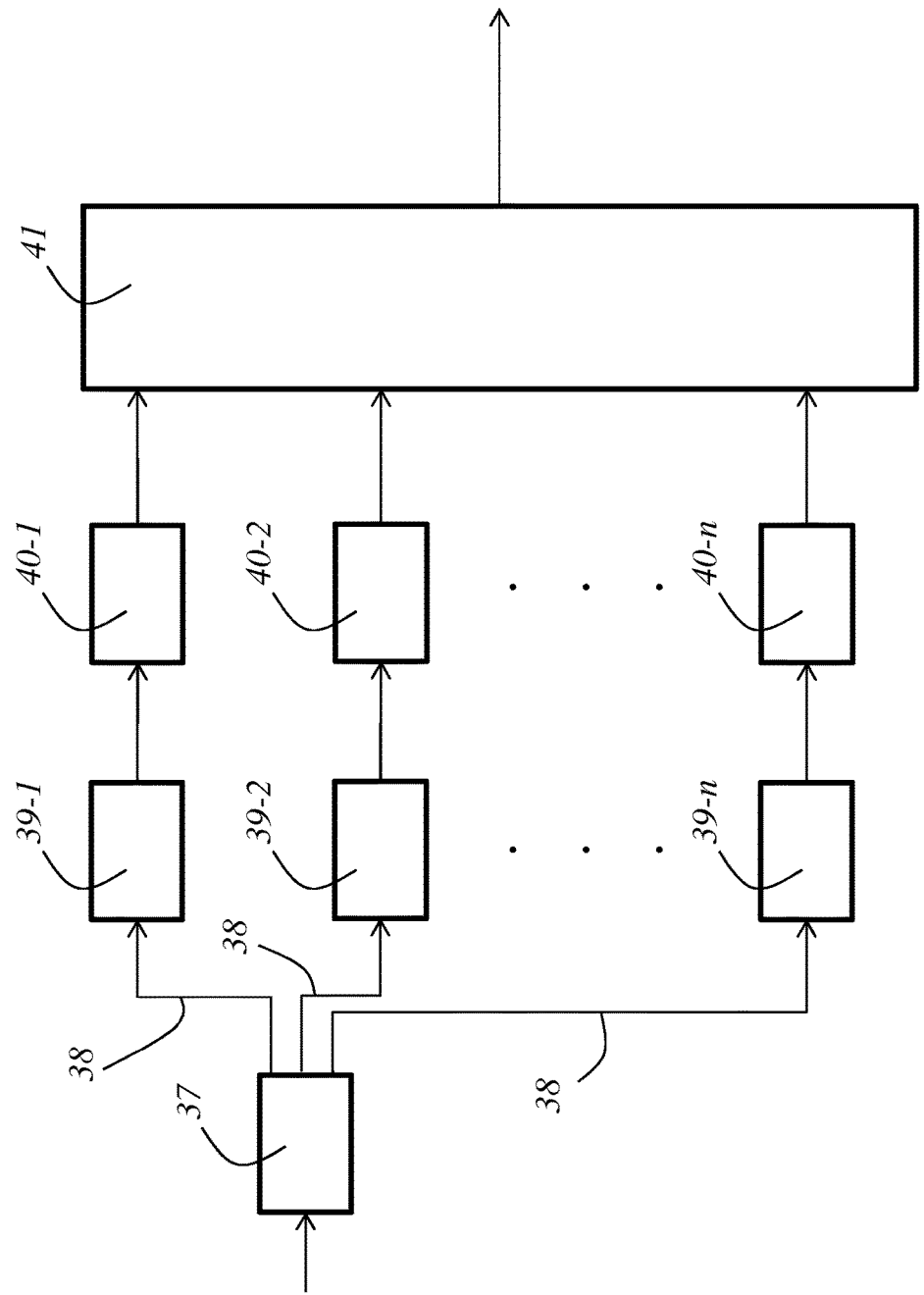
FIG. 6 schematically illustrates the procedures for increasing the time resolution for the sampling of a first and/or a second analog electrical signal.

FIG. 6 schematically illustrates the procedures for increasing the time resolution for the drafting sampling of a first and/or a second analog electrical signal. In the process, the respective analog electrical signal 37 is converted by a comparator 32—as described in detail above—into n identical digital data sequences 38. Each of the digital data sequences 38 is passed through a delay stage 39-1 through 39-n. Delay stages 39-1 through 39-n delay the respective digital data sequences 38 to different degrees. The delay time of the delay stage 39-x differs from the delay time of the next stage 39-(x+1) by a time offset that corresponds to the n-th fraction of a time slot. Then, digital data sequences 38 are each delivered to respective serial-to-parallel converters 40-1 through 40-n, which generate respective digital data words. These data words are then mathematically combined in a combining and correlating unit 41.

LIST OF REFERENCE NUMERALS 1 scanning microscope
2 light source 3 pulsed laser
4 primary light beam
5 beam splitter
6 measurement beam
7 excitation detector
8 excitation beam
9 control device
10 illumination pinhole
11 main beam splitter
12 scanning device
13 scanning mirror
14 scanning optics
15 tube optics
16 microscope objective
17 sample
18 detection light
19 detection pinhole
20 detector
21 power-time profile of the excitation light
22 power-time profile of the detection light
23 photon event
24 excitation pulse
25 first digital data sequence
26 second digital data sequence
27 first switching instant
28 second switching instant
29 first serial-to-parallel converter
30 correlating unit
31 constant fraction discriminator
32 comparator
33 second serial-to-parallel converter
34 scan control unit
35 unit
36 memory
37 electrical signal
38 digital data sequence
39 delay stage
40 serial-to-parallel converter
41 combining and correlating unit
42 first constant fraction discriminator
43 first comparator

What is claimed is:

1. A method for measuring a fluorescence lifetime of an excited state in a sample, comprising the following steps:
   (a) generating an excitation pulse and illuminating a sample region with the excitation pulse,
   (b) generating a first digital data sequence which is representative of a power-time profile of the excitation pulse,
   (c) detecting a detection light emanating from the sample region with a detector,
   (d) generating a second digital data sequence, said second digital data sequence being representative of a power-time profile of the detection light,
   (e) determining a first switching instant from the first digital data sequence, wherein the first switching instant
       (i) occurs when there is a first change from a lower standardized signal to an upper standardized signal or a second change from an upper standardized signal to a lower standardized signal within the first digital data sequence and/or within a first data word, or
       (ii) is calculated from the first change from the lower standardized signal to the upper standardized signal or from the second change from the upper standardized signal to the lower standardized signal within the first data sequence and/or within the first data word, wherein the first switching instant is calculated as an arithmetic mean of time intervals between the first change and the second change within the first digital data sequence and/or within the first data word,
   (f) determining a second switching instant from the second digital data sequence, and
   (g) calculating a time difference between the first and second switching instants.

2. The method as recited in claim 1, wherein
   (a) the steps (a) through (g) are cyclically repeated and/or
   (b) the steps (a) through (g) are cyclically repeated at a constant repetition frequency.

3. The method as recited in claim 1, wherein the excitation pulse originates from a primary light pulse, a portion of which is delivered to an excitation detector which generates a first analog electrical signal whose amplitude-time profile is dependent on the time profile of a power of the portion of the primary light pulse, and, in order to generate the first digital data sequence, the first analog electrical signal is sampled over time in predefined and/or predefinable first time slots.

4. The method as recited in claim 3, wherein the first data sequence is generated from standardized electrical signals in such a way that either a lower standardized signal is generated when the amplitude just sampled is below a defined and/or definable first excitation threshold, or an upper standardized signal which is different from the lower standardized signal is generated when the amplitude just sampled is above a defined and/or definable second excitation threshold.

5. The method as recited in claim 1, wherein the detector generates a second analog electrical signal whose amplitude-time profile is dependent on the time profile of the power of the detection light, and, in order to generate the second digital data sequence, the second analog electrical signal is sampled over time in predefined and/or predefinable second time slots.

6. The method as recited in claim 5, wherein the second data sequence is generated from standardized electrical signals in such a way that either a lower standardized signal is generated when the amplitude just sampled is below a defined and/or definable first detection threshold, or an upper standardized signal which is different from the lower standardized signal is generated when the amplitude just sampled is above a defined and/or definable second detection threshold.

7. The method as recited in claim 3, wherein
   (a) the first and/or the second analog electrical signal is sampled at a sampling frequency which is significantly higher than the repetition frequency and/or
   (b) the first and/or the second analog electrical signal is sampled at a sampling frequency more than 50 times higher than the repetition frequency and/or
   (c) the first and/or the second analog electrical signal is sampled at a sampling frequency about 125 times higher than the repetition frequency and/or
   (d) the first and/or the second analog electrical signal is sampled at a sampling frequency of 10 GHz, while the repetition frequency is 80 MHz.

8. The method as recited in claim 3, wherein in order to increase the time resolution,
   (a) the first analog electrical signal is sampled repeatedly and/or (b) the first analog electrical signal is sampled repeatedly with a continuously adjustable time offset which is shorter than a time slot and/or
(c) the first analog electrical signal is sampled n times, with a time offset that corresponds to an n-th fraction of a time slot and/or
(d) the second analog electrical signal is sampled repeatedly and/or
(e) the second analog electrical signal is sampled repeatedly with a continuously adjustable time offset which is shorter than a time slot and/or
(f) the second analog electrical signal is sampled n times, with a time offset that corresponds to the n-th fraction of a time slot.

9. The method as recited in claim 8, wherein sampling results of multiple samplings are mathematically interleaved to produce the first data sequence and the second data sequence, respectively.

10. The method as recited in claim 1, wherein
the generation of the first digital data sequence is accomplished using a second sampling device including a comparator and/or a constant fraction discriminator
and wherein the first sampling device includes a constant fraction discriminator.

11. The method as recited in claim 1, wherein the first data sequence is converted by a first serial-to-parallel converter into first parallel data words, and/or the second data sequence is converted by a second serial-to-parallel converter into second parallel data words.

12. The method as recited in claim 11, wherein the data words are each representative of a measurement period that is at least as long as a time interval between successive excitation pulses.

13. The method as recited in claim 1, wherein the second switching instant is defined as
occurring when there is a first change from a lower standardized signal to an upper standardized signal or a second change from the upper standardized signal to the lower standardized signal within the second data sequence and/or within a second data word, or
being calculated from the first change from the lower standardized signal to the upper standardized signal or from the second change from the upper standardized signal to the lower standardized signal within the second data sequence and/or within the second data word, wherein the second switching instant is calculated as an arithmetic mean of time intervals between the first change and the second change within the second data sequence and/or within the second data word.

14. The method as recited in claim 1, wherein at least one frequency distribution of a plurality of calculated time differences is generated.

15. The method as recited in claim 1, wherein
(a) different sample regions which are adjacent to each other and/or disposed adjacent to each other in a scan line, are sequentially analyzed one after the other with respect to the lifetime of an excited state and/or
(b) different sample regions which are adjacent to each other and/or disposed adjacent to each other in a scan line, are sequentially analyzed one after the other with respect to the lifetime of an excited state; position information being added to the data sequences and/or data words and/or frequency distributions and/or time differences of each sample region
(c) different sample regions which are adjacent to each other and/or disposed adjacent to each other in a scan line, are sequentially analyzed one after the other with respect to the lifetime of an excited state and a fluorescence lifetime image (FLIM) of the sample is generated.

16. The method as recited in claim 1, wherein a scanning device is used for steering the excitation light and/or the detection light.

17. An apparatus for carrying out a method according to claim 1.

18. An apparatus for measuring a fluorescence lifetime of an excited state in a sample, the apparatus including:
a light source for generating an excitation light including an excitation pulse for illuminating a sample region with the excitation pulse;
a detector for detecting detection light emanating from the sample region;
a scanning device for steering the excitation light and/or the detection light; and
a control device to
(a) generate a first digital data sequence using a first sampling device, said first digital data sequence being representative of a power-time profile of the excitation pulse,
(b) generate a second digital data sequence being representative of a power-time profile of the detection light,
(c) determine a first switching instant from the first digital data sequence,
wherein the control device defines the first switching instant to be when there is a first change from a lower standardized signal to an upper standardized signal or a second change from the upper standardized signal to the lower standardized signal within the first data sequence and/or within a first data word, or
wherein the control device calculates the first switching instant from the first change from the lower standardized signal to the upper standardized signal or from the second change from the upper standardized signal to the lower standardized signal within the first data sequence and/or within the first data word, by calculating an arithmetic mean of time intervals between the first change and the second change within the first data sequence and/or within the first data word,
(d) determine a second switching instant from the second digital data sequence, and
(e) calculate a time difference between the first and second switching instants.

19. The apparatus as recited in claim 18, wherein the light source produces a sequence of excitation pulses, and the control device cyclically repeats the steps a through e.

20. The apparatus as recited in claim 19, wherein the light source generates a primary light beam which is split by a beam splitter into an excitation beam, which includes the excitation pulses, and a measurement beam, and an excitation detector receives the measurement beam and generates a first analog electrical signal whose amplitude-time profile is dependent on the time profile of the power of the measurement beam, and, in order to generate the first digital data sequence, the control device samples the first analog electrical signal over time in predefined and/or predefinable first time slots.

21. The apparatus as recited in claim 19, wherein the control device generates the first data sequence from standardized electrical signals in such a way that either a lower standardized signal is generated when the amplitude just sampled is below a defined and/or definable first excitation threshold, or an upper standardized signal which is different from the lower standardized signal is generated when the amplitude just sampled is above a defined and/or definable second excitation threshold.

22. The apparatus as recited in claim 19, wherein the detector generates a second analog electrical signal whose amplitude-time profile is dependent on the time profile of the power of the detection light and, in order to generate the second digital data sequence, the control device samples the second analog electrical signal over time in predefined and/or predefinable second time slots.

23. The apparatus as recited in claim 19, wherein the control device generates the second data sequence from standardized electrical signals in such a way that either a lower standardized signal is generated when the amplitude just sampled is below a defined and/or definable first detection threshold, or an upper standardized signal which is different from the lower standardized signal is generated when the amplitude just sampled is above a defined and/or definable second detection threshold.

24. The apparatus as recited in claim 21, wherein the control device
   (a) samples the first and/or the second analog electrical signal at a sampling frequency which is significantly higher than the repetition frequency and/or
   (b) samples the first and/or the second analog electrical signal at a sampling frequency more than 50 times higher than the repetition frequency and/or
   (c) samples the first and/or the second analog electrical signal at a sampling frequency about 125 times higher than the repetition frequency and/or
   (d) samples the first and/or the second analog electrical signal at a sampling frequency of 10 GHz, while the repetition frequency is 80 MHz.

25. The apparatus as recited in claim 21, wherein in order to increase the time resolution, the control device
   (a) samples the first analog electrical signal repeatedly and/or
   (b) samples the first analog electrical signal repeatedly, with a time offset shorter than a time slot and/or
   (c) samples the first analog electrical signal n times, with a time offset that corresponds to an n-th fraction of a time slot and/or
   (d) samples the second analog electrical signal repeatedly and/or
   (e) samples the second analog electrical signal repeatedly, with a time offset shorter than a time slot and/or
   (f) samples the second analog electrical signal n times, but with a time offset that corresponds to the n-th fraction of a time slot.

26. The apparatus as recited in claim 25, wherein the control device mathematically interleaves sampling results of multiple samplings to produce the first data sequence and the second data sequence, respectively.

27. The apparatus as recited in claim 19, wherein
   the generation of the first digital data sequence is accomplished using the first sampling device including a comparator and/or a constant fraction discriminator and/or
   wherein the second sampling device includes a constant fraction discriminator.

28. The apparatus as recited in claim 19, wherein a first serial-to-parallel converter is provided to convert the first data sequence into first parallel data words and/or a second serial-to-parallel converter is provided to convert the second data sequence into second parallel data words.

29. The apparatus as recited in claim 19, wherein the first and/or the second serial-to-parallel converter generates data words which are each representative of a measurement period which is at least as long as a time interval between successive excitation pulses.

30. The apparatus as recited in claim 19, wherein
   (a) the control device defines the second switching instant to be when there is a first change from a lower standardized signal to an upper standardized signal or a second change from the upper standardized signal to the lower standardized signal within the second data sequence and/or within a second data word or
   (b) the control device calculates the second switching instant from the first change from the lower standardized signal to the upper standardized signal and from the second change from the upper standardized signal to the lower standardized signal within the second data sequence and/or within a second data word by calculating an arithmetic mean of time intervals between the first change and the second change within the second digital data sequence and/or within the second data word.

31. The apparatus as recited in claim 19, wherein the control device generates at least one frequency distribution of a plurality of calculated time differences.

32. The apparatus as recited in claim 19, wherein
   (a) the scanning device is provided for directing the excitation light to different sample locations and/or for scanning the sample and/or
   (b) the scanning device is provided for directing the excitation light to different sample locations and/or for scanning the sample, the control device adding position information regarding a position of the scanning device to the data sequences and/or data words and/or frequency distributions and/or time differences of each sample region.

33. The apparatus as recited in claim 19, wherein the control device and/or at least one of the first or second sampling devices and/or at least one of the serial-to-parallel converters forms part of a programmable integrated circuit.

34. The apparatus as recited in claim 19, wherein the apparatus forms part of a scanning microscope.

35. A scanning microscope comprising an apparatus according to claim 19.

* * * * *